US007217524B2

(12) United States Patent
Suzu et al.

(10) Patent No.: US 7,217,524 B2
(45) Date of Patent: *May 15, 2007

(54) METHOD FOR DIAGNOSING APLASIA OF CORPUS CALLOSUM

(75) Inventors: Shinya Suzu, Zama (JP); Hiroaki Hageshita, Zama (JP); Kouji Nomaguchi, Zama (JP); Muneo Yamada, Zama (JP); Hirotoshi Hayasawa, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/409,216

(22) Filed: Apr. 21, 2006

(65) Prior Publication Data

US 2006/0178337 A1 Aug. 10, 2006

Related U.S. Application Data

(62) Division of application No. 10/314,395, filed on Dec. 6, 2002, now Pat. No. 7,081,338.

(30) Foreign Application Priority Data

Dec. 20, 2001 (JP) ............................. 2001-387853
Jul. 18, 2002 (JP) ............................. 2002-209457

(51) Int. Cl.
 *C12Q 1/68* (2006.01)
 *C12P 19/34* (2006.01)
 *C07H 21/02* (2006.01)

(52) U.S. Cl. .................... 435/6; 435/91.2; 536/23.1
(58) Field of Classification Search ............... None
 See application file for complete search history.

(56) References Cited

FOREIGN PATENT DOCUMENTS

| EP | 1 211 313 A2 | 6/2002 |
|----|---|---|
| JP | 11-018622 | 1/1999 |
| WO | WO 98/45434 | 10/1998 |
| WO | WO 00/00604 | 1/2000 |
| WO | WO 01/54474 | 8/2001 |
| WO | WO 01/54708 | 8/2001 |
| WO | WO 01/55315 | 8/2001 |
| WO | WO 01/75067 | 10/2001 |

OTHER PUBLICATIONS

XP-002234524, Jan. 10, 2002, Abstract (WO 0154474 A) (EBI Database Accession No. ABB10359).
XP-002234525, Nov. 7, 2001, Abstract (WO 0155315 A) (EBI Database Accession No. AAU18038).
XP-002234526, Oct. 8, 2001, Abstract (EBI Database Accession No. BI830026).
Geneseq Assession No. ABA06581 dated Jan. 10, 2002.
Geneseq Assession No. AAS28826, dated Nov. 7, 2001.
Geneseq Assession No. ABA06752, dated Jan. 10, 2002.
Geneseq Assession No. AAS28873, dated Nov. 7, 2001.
Geneseq Assession No. ABB10530, dated Jan. 10, 2002.
Geneseq Assession No. AAU18085, dated Nov. 7, 2001.
Geneseq Assession No. AAU18038, dated Nov. 7, 2001.
Geneseq Assession No. ABB10359, dated Jan. 10, 2002.
Geneseq Assession No. ABG16751, dated Feb. 18, 2002.
Fechner, et al. "Expression of Coxsackie Adenovirus Receptor and Alpha$_v$-integrin Does Not Correlate with Adenovector Targeting In Vivo Indicating Anatomical Vector Barriers," *Gene Therapy*, vol. 6, No. 9, pp. 1520-1535, 1999.
Suzu, et al. Molecular Cloning of a Novel Immunoglobulin Superfamily Gene Preferentially Expressed by Brain and Testis, *Biochemical and Biophysical research Communications*, vol. 296, No. 5, pp. 1215-1221, 2002.
European Search Report, dated Mar. 13, 2003, corresponding to a related European patent application.
Cyr, et al. "Identification and Developmental Regulation of Cadherin Messenger Ribonucleic Acids in the Rat Testis," *Endocrinology*. vol. 131, No. 1, pp. 139-145, 1992.
Genuardi, et al. "A New Case of Interstitial Deletion of Chromosome 3q, del(3q)(q13.12q21.3) with Agenesis of the Corpus Callosum," *Clinical Dysmorphology*, vol. 3, pp. 292-296, 1994.
Kamiguchi, et al. "Adhesion Molecules and Inherited Diseases of the Human Nervous System," *Annual Review of Neuroscience*, vol. 21, pp. 97-125, 1998.
Ogilvie, et al. "Deletion of Chromosome 3q Proximal Region Gives Rise to a Variable Phenotype," *Clinical Genetics*, vol. 53, pp. 220-222, 1998.
Roche Diagnostics GmbH, Expand Long Template PCR System Jun. 2002.
Buck, et al. Design strategies and performance of custom DNA sequencing primers. Biotechniques. Sep. 1999; 27(3):528-36.
Ginzinger, DG. Gene quantification using real-time quantitative PCR: an emerging technology hits the mainstream. Exp Hematol. Jun. 2002;30(6):503-12.
Kuromitsu, et al. A unique downregulation of h2-calponin gene expression in Down syndrome : a possible attenuation mechanism for fetal survival by methylation at the CpG island in the trisomic chromosome 21, Molecular and Cellular Biology, vol. 17, No. 2, pp. 707-712, Feb. 1997.

*Primary Examiner*—Jeffrey Fredman
*Assistant Examiner*—Samuel Woolwine
(74) *Attorney, Agent, or Firm*—Knobbe, Martens, Olson & Bear, LLP

(57) ABSTRACT

Aplasia of the corpus callosum or aspermatogenesis is diagnosed by investigating existence or expression of the BT-IgSF gene with use of a primer for PCR or probe for hybridization comprising a DNA coding for a novel cell adhesion molecule (BT-IgSF) defined in the following (A) or (B) or a partial sequence thereof:

(A) a protein comprising the amino acid sequence of the amino acid numbers 1 to 409 of SEQ ID NO: 2;

(B) a protein comprising an amino acid sequence of the amino acid numbers 1 to 409 of SEQ ID NO: 2 including substitution, deletion, insertion or addition of one or several amino acids and having a function as a cell adhesion molecule.

3 Claims, 1 Drawing Sheet

METHOD FOR DIAGNOSING APLASIA OF CORPUS CALLOSUM

RELATED APPLICATIONS

This application is a divisional of U.S. application Ser. No. 10/314,395, filed Dec. 6, 2002, now U.S. Pat. No. 7,081,338, which claims priority of Japanese Patent Application No. 2001-387853, filed Dec. 20, 2001 and Japanese Patent Application No. 2002-209457, filed Jul. 18, 2002. Each of the above applications are incorporated herein by reference in their entirety.

FIELD OF THE INVENTION

The present invention relates to a novel protein estimated to be a cell adhesion molecule involved in development of the corpus callosum and spermatogenesis and a gene coding for the same as well as use of the protein and the gene. The protein and the gene of the present invention are useful in pharmaceutical and diagnostic fields.

DESCRIPTION OF THE RELATED ART

It is well known that, upon development of various organs of organisms, protein molecules on surfaces of cells constituting organs (cell adhesion molecules) play an important role. It has been found that these cell adhesion molecules are closely associated with important reactions in organisms such as recognition of immune cells, inflammation and metastasis of cancer.

The cell adhesion molecules are primarily classified into integrin, cadherin, selectin, immunoglobulin superfamily and CD44 family depending on their structures. Of these, the immunoglobulin superfamily is a group of molecules that have a structure similar to immunoglobulin, and an enormous number of proteins belong to this family and exert a wide variety of functions. For example, molecules that carry out signal transduction associated with cell adhesion are known. There are also protein molecules known as cytokine receptors and protein molecules known as virus receptors. Some are also known as protein molecules existing on cell surfaces that regulate cell functions, typically immunological functions. Further, many proteins belonging to the immunoglobulin superfamily are expected to play important roles in morphogenesis and development of organs in organisms as cell adhesion molecules. However, tissues or cells constituting a tissue in which each protein is expressed significantly differ depending on individual proteins and cannot be easily inferred by analysis of primary sequence (amino acid sequence) of the proteins.

Meanwhile, there are known cases presenting predominant symptoms of facial malformation, mental retardation, speech disorder and so forth due to aplasia of the corpus callosum (Genuardi, M., Calvieri, F., Tozzi, C., Coslovi, R., Neri, G., A new case of interstitial deletion of chromosome 3q, del(3q)(q13.12q21.3), with aplasia of the corpus callosum, Clinical Dysmorphology, 3, 292–296, 1994; Ogilvie, C. M., Rooney, S. C., Hodgson, S. V., Berry, A. C., Deletion of chromosome 3q proximal region gives to a variable phenotype, Clinical Genetics, 53, 220–222, 1998), and these cases are considered to be caused by deletion of the chromosome 3. However, its causative gene has not been identified, and hence no treatment method has been established.

SUMMARY OF THE INVENTION

An object of the present invention is to isolate a gene coding for a novel cell adhesion molecule and provide a technique concerning the utilization of this gene.

The inventors of the present invention searched a known database for a gene having homology to the amino acid sequence of the extracellular region of macrophage colony stimulating factor (M-CSF) receptor and isolated a cDNA of the gene having the found sequence. As a result of analysis of expression of the gene, they found that this gene was highly expressed in the testis and brain, in particular, in the corpus callosum, and accomplished the present invention.

That is, the present invention provides the followings.

(1) A DNA which codes for a protein defined in the following (A) or (B):

(A) a protein comprising the amino acid sequence of the amino acid numbers 1 to 409 of SEQ ID NO: 2;

(B) a protein comprising an amino acid sequence of the amino acid numbers 1 to 409 of SEQ ID NO: 2 including substitution, deletion, insertion or addition of one or several amino acids and having a function as a cell adhesion molecule.

(2) The DNA according to (1), which codes for a protein comprising the amino acid sequence of SEQ ID NO: 2 or an amino acid sequence of SEQ ID NO: 2 including substitution, deletion, insertion or addition of one or several amino acids.

(3) The DNA according to (1), which is a DNA defined in the following (a) and (b):

(a) a DNA comprising the nucleotide sequence of the nucleotide numbers 67–1296 of SEQ ID NO: 1;

(b) a DNA which is hybridizable with the nucleotide sequence of the nucleotide numbers 67 to 1296 of SEQ ID NO: 1 under the stringent conditions and codes for a protein functioning as a cell adhesion molecule.

(4) A DNA which comprises the nucleotide sequence of SEQ ID NO: 1 or a partial sequence thereof and which is used as a primer for PCR or a probe for hybridization for investigating existence or expression of a gene corresponding to the nucleotide sequence of SEQ ID NO: 1.

(5) The DNA according to (4), which is used for diagnosis of aplasia of the corpus callosum.

(6) The DNA according to (4), which is used for diagnosis of aspermatogenesis.

(7) The DNA according to any one of (4) to (6), which comprises a set of a DNA having the nucleotide sequence of SEQ ID NO: 8 and a DNA having the nucleotide sequence of SEQ ID NO: 9.

(8) A medicament for gene therapy which comprises a DNA coding for the amino acid sequence of SEQ ID NO: 1 and which is used for treatment of aplasia of the corpus callosum.

(9) A medicament for gene therapy which comprises a DNA coding for the amino acid sequence of SEQ ID NO: 1 and which is used for treatment of aspermatogenesis.

(10) A protein defined in the following (A) or (B):

(A) a protein comprising the amino acid sequence of the amino acid numbers 1 to 409 of SEQ ID NO: 2;

(B) a protein comprising an amino acid sequence of the amino acid numbers 1 to 409 of SEQ ID NO: 2 including substitution, deletion, insertion or addition of one or several amino acids and having a function as a cell adhesion molecule.

(11) A medicament comprising the protein according to (10) or a salt thereof.

(12) The medicament according to (11), which is used for treatment of aplasia of the corpus callosum.

(13) The medicament according to (11), which is used for treatment of aspermatogenesis.

The protein of the present invention was identified as a protein molecule belonging to the immunoglobulin superfamily based on its structure, and designated as "BT-IgSF (brain and testis-specific immunoglobulin superfamily)" protein.

The present invention provides a novel cell adhesion molecule, a BT-IgSF protein, and a DNA coding for the protein. The BT-IgSF protein and a DNA coding for the protein are useful for treatment and diagnosis of aplasia of the corpus callosum or aspermatogenesis.

DETAILED DESCRIPTION OF THE PREFERRED EMBODIMENTS

Figure 1:
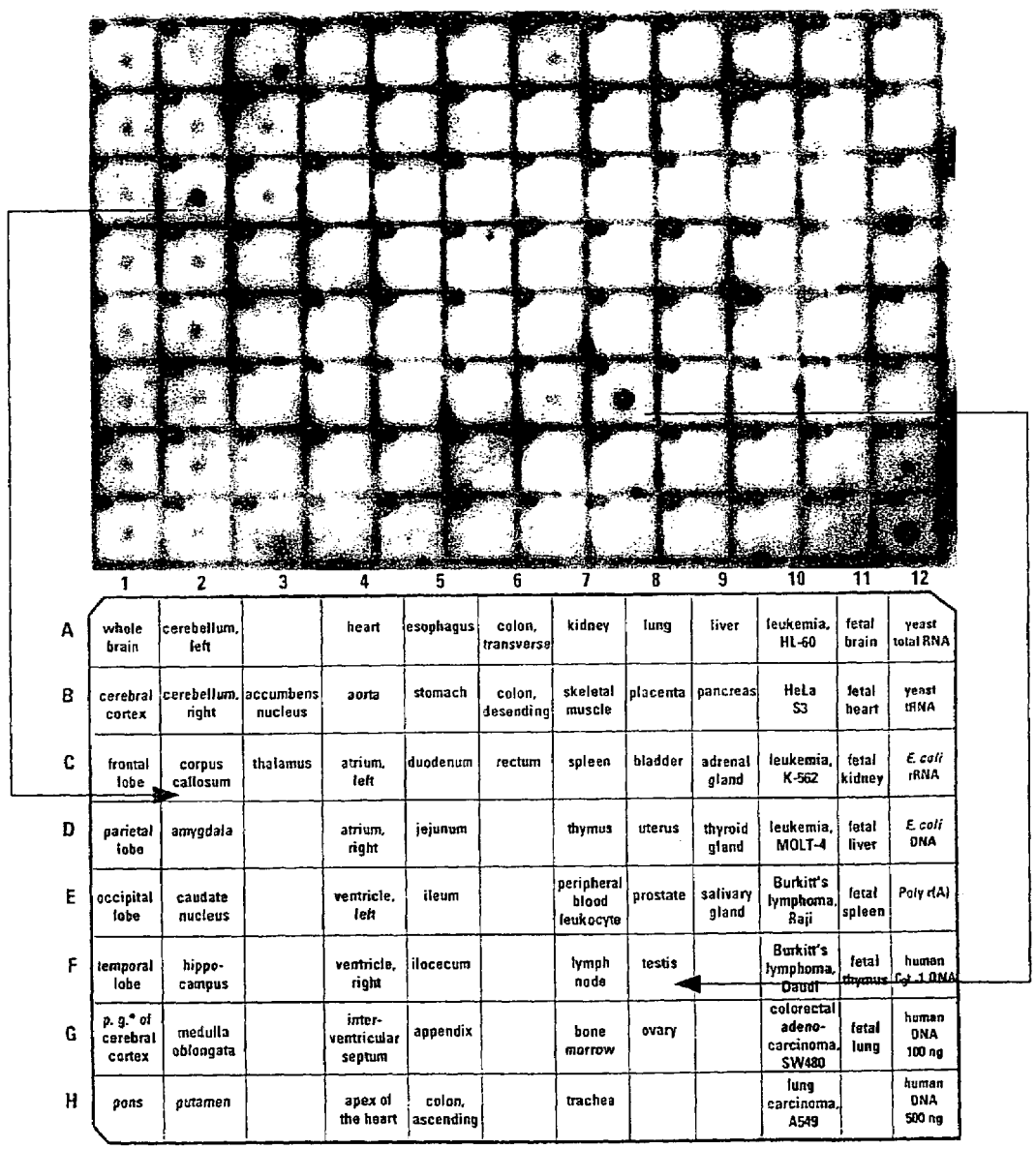
FIG. 1 (photograph) shows results of Northern hybridization using a cDNA fragment of the human BT-IgSF gene as a probe.

Hereafter, the present invention will be explained in more detail.

The DNA of the present invention is a DNA coding for a protein defined in the following (A) or (B):

(A) a protein comprising the amino acid sequence of the amino acid numbers 1 to 409 of SEQ ID NO: 2;

(B) a protein comprising an amino acid sequence of the amino acid numbers 1 to 409 of SEQ ID NO: 2 including substitution, deletion, insertion or addition of one or several amino acids and having a function as a cell adhesion molecule.

The DNA of the present invention can be obtained by amplifying mRNA derived from the human kidney by polymerase chain reaction (PCR, White, T. J. et al., Trends Genet., 5, 185, 1989) as described later. Further, since the nucleotide sequence of cDNA of the BT-IgSF gene has been elucidated by the present invention, the DNA fragment of the present invention can also be obtained by chemical synthesis. Further, a genomic gene for the BT-IgSF protein can be obtained by performing PCR using human chromosomal DNA as a template. The BT-IgSF gene derived from chromosome is expected to include one or more introns in the coding region, but even such a DNA interrupted with intron(s) also falls within the scope of the DNA of the present invention so long as it codes for the BT-IgSF protein.

As a raw material for obtaining cDNA coding for the BT-IgSF protein, although any of human organs or established cell lines producing the BT-IgSF protein can be utilized, specifically, the kidney can be mentioned. Further, cDNA derived from the testis of an animal such as mouse can also be used as a raw material for obtaining a homologue of the BT-IgSF gene. Messenger RNA (mRNA) is prepared from cells of tissues of such organs in a conventional manner (Sambrook, J. et al., Molecular Cloning, Vol. 3, Ed. 2, Cold Spring Harbor Laboratory Press, 1989). Further, mRNA derived from the human kidney is commercially available (Clontech, #6538-1) and can be preferably used in the present invention. A single-stranded cDNA is prepared by using the obtained mRNA as a template and a reverse transcriptase.

Various oligonucleotides are chemically synthesized as 5' end primers and 3' end primers for the BT-IgSF gene, then these primers, the single-stranded cDNA and Taq DNA polymerase are used to amplify the DNA fragment by PCR, and a DNA fragment having a target size is prepared by agarose gel electrophoresis. The nucleotide sequence of the prepared DNA fragment can be directly determined. Examples of the primers used for PCR include oligonucleotides having the nucleotide sequences of SEQ ID NOS: 8 and 9. If PCR is performed by using these primers and mRNA or cDNA library derived from a human tissue as a template, there can be obtained a DNA having one nucleotide of G at the 5' end and a sequence of GACATGAGG at the 3' end in addition to the sequence of SEQ ID NO: 1.

Further, the nucleotide sequence can also be determined by inserting an amplified fragment into an appropriate commercially available plasmid vector such as pCR2.1, pCRII (both from Invitrogen) or pUC118 (Takara Shuzo), transforming *Escherichia coli* such as INValphaF' (Invitrogen) or HB101 (Takara Shuzo) and purifying the plasmid.

The result of determination of the nucleotide sequence of DNA of the present invention in a conventional manner is shown in SEQ ID NO: 1, and the amino acid sequence encoded by this DNA is shown in SEQ ID NO: 2.

As a result of search of the amino acid sequence of SEQ ID NO: 2 using Simple Modular Architecture Research Tool (SMART, see Schulta, J., Copley, R. R., Doerks, T., Ponting, C. P., Bork, P., SMART: A web-based tool for the study of genetically mobile domains, Nucleic Acids Research, 28 (1), 231–234, 2000; http://smart.embl-heidelberg.de), this sequence was found to be constituted by a signal peptide, extracellular region, transmembrane region and intracellular region from the N-terminus side. Of these, the signal sequence was expected to comprise the residues of the amino acid numbers −22 to −1 of SEQ ID NO: 2. Therefore, the matured protein of BT-IgSF is expected to correspond to the amino acid numbers 1 to 409 of SEQ ID NO: 2.

On the other hand, in an analysis using the PSORT (Nakai, K., "Prediction of structure and function of proteins", Idensi Igaku (Genetic Medicine), Vol. 4, 3, 377–382, 2000; http://psort.nibb.ac.jp) as an analysis program, the signal sequence was expected to comprise the residues of the amino acid numbers −22 to −2 of SEQ ID NO: 2.

Based on the above, the matured protein of BT-IgSF is expected to correspond to the residues of the amino acid numbers 1 to 409 or the amino acid numbers −1 to 409 of SEQ ID NO: 2. In either case, the matured protein of BT-IgSF includes the residues of the amino acid numbers 1 to 409.

In addition, the transmembrane region was expected to comprise the residues of the amino acid numbers 224 to 246 in the analysis by SMART and the residues of the amino acid numbers 228 to 244 in the analysis by PSORT.

The DNA of the present invention is a DNA fragment coding for a BT-IgSF precursor having the amino acid sequence of SEQ ID NO: 2 (amino acid numbers −22 to 409) or an amino acid sequence of the amino acid numbers 1 to 409 or the amino acid numbers −1 to 409 of SEQ ID NO: 2. In the present invention, the matured BT-IgSF protein may be added with a methionine residue at the N-terminus of the amino acid sequence of the amino acid numbers 1 to 409 or the amino acid numbers −1 to 409 of SEQ ID NO: 2.

In the present invention, the BT-IgSF protein may include substitution, deletion, insertion or addition of one or more amino acid residues so long as the activity as the BT-IgSF protein, that is, a function as a cell adhesion molecule, is not substantially deteriorated. A DNA coding for any of these BT-IgSF proteins also falls within the scope of the present invention. Specific examples of such a DNA fragment include a DNA fragment comprising the nucleotide sequence of the nucleotide numbers 1 to 1296 of SEQ ID NO: 1 and a DNA fragment comprising the nucleotide sequence of the nucleotide numbers 67 to 1296 of SEQ ID NO: 1. Further, sequences in which a codon for each amino acid is replaced with an equivalent codon are also encompassed in the scope of the present invention so long as the nucleotide sequences code for the same amino acid sequence.

A DNA coding for a protein substantially the same as such BT-IgSF proteins as mentioned above can be obtained by, for example, the site-directed mutagenesis to modify the nucleotide sequence so that amino acid residues at a specific site should include substitution, deletion, insertion, addition or inversion. Further, such a DNA can also be obtained by treating a DNA coding for a BT-IgSF protein by a mutagenizing agent or the like to randomly introduce a mutation. A DNA coding for a protein substantially the same as the BT-IgSF proteins can be obtained by expressing such a DNA introduced with a mutation in an appropriate cell and investigating activity of the expression product as a cell adhesion molecule. Further, a DNA coding for a protein substantially the same as the BT-IgSF proteins can also be obtained by isolating a DNA that is hybridizable with DNA having, for example, the nucleotide sequence of the nucleotide numbers 1 to 1296 or the nucleotide sequence of the nucleotide numbers 67 to 1296 of SEQ ID NO: 1 in Sequence Listing under the stringent conditions, and codes for a protein having a function as a cell adhesion molecule from a cell harboring a DNA coding for a BT-IgSF protein having a mutation. The "stringent conditions" referred to herein includes a condition under which a so-called specific hybrid is formed, and a non-specific hybrid is not formed. For example, the stringent conditions include a condition under which two of DNA's having homology of not less than 20%, preferably not less than 50%, more preferably not less than 80%, are hybridized with each other, and two of DNA's having homology lower than the above are not hybridized with each other. Specifically, the stringent conditions are exemplified by a condition under which two of DNA's are hybridized with each other at a salt concentration corresponding to 0.2×SSC, 0.1% SDS at 42° C., preferably 0.1×SSC, 0.1% SDS at 68° C.

A method for preparing a BT-IgSF protein will be explained hereafter. A large amount of a BT-IgSF protein can be prepared by, for example, inserting total DNA or a part of the DNA into an appropriate expression vector having a promoter sequence, marker gene, replication origin and so forth in a conventional manner and introducing the vector into a microorganism, cultured cell or animal or plant cell to express the vector. A variety of such expression vectors are commercially available and can be used for the present invention. When expression of a matured BT-IgSF protein is intended, a DNA fragment coding for the amino acid sequence of the amino acid numbers 1 to 409 of SEQ ID NO: 2 in which an initiation codon (ATG) is added to the 5' end, a termination codon is added to the 3' end and restriction enzyme recognition sequences are added outside these codons can be inserted into the vector downstream from the promoter sequence. To add these codons and restriction enzyme recognition sequences to the DNA of the present invention, oligonucleotide primers used for amplification of the DNA by PCR can be designed to contain the aforementioned codons and restriction enzyme recognition sequences. When the expressed BT-IgSF protein is accumulated in a microbial cell as inclusion bodies, they can be solubilized with a 8 M urea solution, 6 M guanidine hydrochloride solution or the like, purified by column chromatography and refolded to produce a BT-IgSF protein having a structure the same as or similar to a naturally occurring protein.

Further, a BT-IgSF protein can be expressed by, for example, inserting a DNA coding for the BT-IgSF protein into a plasmid having an adenovirus promoter, DHFR (dehydrofolic acid reductase) gene, SV40 poly-A sequence and replication origin by ligation, introducing the obtained plasmid into a DHFR-deficient CHO cell (cell derived from Chinese hamster) by a calcium phosphate method or the like and culturing the cell in MTX (methotrexate) medium. In this case, although a matured BT-IgSF protein may be directly expressed, a precursor protein may be expressed by introducing a DNA coding for the BT-IgSF precursor having a signal sequence into the cell. When the expressed protein is accumulated as a soluble protein in a cell culture medium, the BT-IgSF protein can be obtained by concentrating the medium using an ultrafiltration membrane and purifying the protein by column chromatography in a conventional manner.

The function as a cell adhesion molecule of BT-IgSF protein prepared by recombinant DNA techniques and purified by column chromatography or the like can be confirmed by the cell aggregation assay (K. Hirata, et al., Cloning of an immunoglobulin family adhesion molecule selectively expressed by endothelial cells, Journal of Biological Chemistry, 276, 16223–16231, 2001) or the like.

As shown in the examples described later, it has been demonstrated that BT-IgSF proteins are expressed in the testis and the brain, in particular, in the corpus callosum in the brain most strongly. Therefore, a BT-IgSF protein is expected to function as a cell adhesion molecule involved in the development of the corpus callosum based on its extremely unique characteristic that its expression is limited in the corpus callosum in the brain. Further, the position of the BT-IgSF gene on the human chromosome was searched in the public human genome database. As a result, it was found that the BT-IgSF gene located on the human chromosome 3 (3q12–23).

The sequence corresponding to the BT-IgSF gene in the database was interrupted by at least 5 introns, and the sequences of the coding region and exons were unknown. However, since the coding sequence of the BT-IgSF gene has been elucidated by the present invention, the functional structure of the genomic gene has also been elucidated.

Based on the above, reports about cases where aplasia of the corpus callosum was considered to be caused by deletion of a region on the chromosome 3 in which presence of the BT-IgSF gene was elucidated were searched for. As a result, it was found that three of such cases had been reported to date (Genuardi, M., Calvieri, F., Tozzi, C., Coslovi, R., Neri, G., A new case of interstitial deletion of chromosome 3q, del(3q)(q13.12q21.3), with aplasia of the corpus callosum, Clinical Dysmorphology, 3, 292–296, 1994; Ogilvie, C. M., Rooney, S. C., Hodgson, S. V., Berry, A. C., Deletion of chromosome 3q proximal region gives to a variable phenotype, Clinical Genetics, 53, 220–222, 1998). These cases showed predominant symptoms of facial malformation, mental retardation, speech disorder and so forth due to aplasia of the corpus callosum, which were considered to be caused by deletion of the chromosome 3. However, the causative gene is still unidentified and hence no treatment method has been established. Since the BT-IgSF gene identified by the present invention is a gene that exists in the aforementioned deleted region and prominently expressed in the corpus callosum, and moreover it is a cell adhesion molecule, which is considered to be important for development of the corpus callosum, this gene is very likely to be a causative gene of these cases.

Therefore, the BT-IgSF gene is considered to be useful for diagnosis of corpus callosum aplasia cases. For example, a disease associated with aplasia of the corpus callosum can be diagnosed by investigating existence or expression of the BT-IgSF gene by using PCR primers or hybridization probe containing the nucleotide sequence of SEQ ID NO: 1 or a partial sequence thereof. Specifically, the existence or structure of the BT-IgSF gene can be confirmed by PCR using chromosomal DNA of a subject as a template and the aforementioned primers or hybridization using the chromosomal DNA and the aforementioned probe. Further, expression of the BT-IgSF gene can be examined by performing PCR or hybridization using mRNA extracted from an appropriate tissue. When the BT-IgSF gene is deficient or is not expressed even though it is not deficient, onset of the diseases is suspected based on such a fact.

As the aforementioned primers, for example, oligonucleotides having the nucleotide sequences of SEQ ID NOS: 8 and 9 can be mentioned. In addition to these primers, primers can be prepared from an arbitrary part in the sequence of SEQ ID NO: 1. Further, the BT-IgSF gene may also be useful as an agent for gene therapy containing this gene or a vector incorporated with this gene in treatment of the aforementioned cases. Further, the BT-IgSF protein itself can be used for treatment of aplasia of the corpus callosum or the like.

Further, as the aforementioned hybridization method, for example, the in situ hybridization method can be specifically mentioned. The probe can be prepared by inserting cDNA of the BT-IgSF gene into a vector such as pCR2.1 vector (Invitrogen) and performing in vitro RNA transcription in a conventional manner. In this case, if a labeled probe is prepared by using digoxigenin or the like, a tissue section can be stained by using such a probe (Murase, S., Hayashi, Y., Expression pattern and neurotropic role of the c-fms proto-oncogene M-CSF receptor in rodent purkinje cells, The Journal of Neuroscience, 24, 10484–10492, 1998).

Further, since the BT-IgSF gene has a characteristic that its expression is limited to the testis apart from some tissues in the brain as mentioned above, it is expected to function as a cell adhesion molecule involved in adhesion between cells in the testis. The seminiferous tubule of the testis is a place of spermatogenesis, where a spermatogonium differentiates into a spermatocyte, resulting in spermatogenesis. While hormones are important in this sperm maturation process, it is widely known that nursing cells also play an important role. The nursing cell is considered to function by directly adhering to a spermatogonium or spermatocyte and is expected to require a cell adhesion molecule for this adhesion. In fact, it has been reported that some cell adhesion molecules are expressed in the testis. For example, N-cadherin is a well-known cell adhesion molecule and it has been reported that it is also expressed in the testis. However, its role in spermatogenesis has not been elucidated so far (Cyr, D. G., Blaschuk, O. W., Robaire, B., Identification and developmental regulation of cadherin messenger ribonucleic acids in the rat testis, Endocrinology, 131, 139–145, 1992).

Since a BT-IgSF protein is obviously a cell adhesion molecule based on its structure and is specifically expressed in the testis, this protein is strongly expected to contribute to, for example, adhesion between nursing cells and spermatogoniums or between nursing cells and spermatocytes and play an important role in spermatogenesis. Therefore, the BT-IgSF gene is considered to be also useful for diagnosis and treatment of aspermatogenesis.

Expression of the BT-IgSF gene in the testis, in particular, in the seminiferous tubule, can be confirmed in the same manner as in the confirmation of the expression of the BT-IgSF gene in the corpus callosum described above.

Further, an agent for gene therapy containing the BT-IgSF gene or a vector incorporated with this gene or the BT-IgSF protein itself can be used in treatment of aspermatogenesis or the like.

Furthermore, since the amino acid sequence of BT-IgSF protein and the nucleotide sequence of the gene coding for the same have been elucidated by the present invention, BT-IgSF gene homologues in other animals can be easily obtained based on this information. A model animal deficient in the BT-IgSF gene can be prepared by using the BT-IgSF gene of the present invention or its homologue.

EXAMPLES

The present invention will be explained more specifically with reference to the following examples.

<1> Search and Isolation of Gene Coding for Amino Acid Sequence Having Homology to Amino Acid Sequence of Extracellular Region of M-CSF Receptor Based on the amino acid sequence of the extracellular region of the M-CSF receptor, an expressed sequence tag (EST) clone coding for an amino acid sequence having homology to the sequence was searched in a database. As the database, the mouse EST database of the National Center for Biotechnology Information (http://www.ncbi.nlm.nih.gov/BLAST/) was used, and tblastn was used as the homology search program (see Altschul, S. F., Madden, T. L., Scaffer, A. A., Zhang, J., Miller, W., Lipman, D. J., Gapped BLAST and PSI-BLAST: A new generation of protein database search programs, Nucleic Acids Research, 25 (17), 3389–3402, 1997).

As a result of the search, one mouse EST clone (#BF236252) was obtained. In the EST database, nucleotide sequences of cDNAs randomly extracted are roughly determined are registered, and the nucleotide sequences of individual cDNAs lack accuracy. Further, the registered sequences do not reflect complete mRNA sequences, but only parts thereof are registered. Therefore, the gene fragment was accurately sequenced based on the sequence of #BF236252. Specifically, the sequencing was performed as follows.

Based on the nucleotide sequence of the aforementioned EST clone (#BF236252), oligonucleotides having the nucleotide sequences of SEQ ID NOS: 3 and 4 were prepared. Then, a cDNA fragment corresponding to the EST clone was amplified by PCR using the oligonucleotides as primers and cDNA derived from the mouse testis (Clontech, Catalog No. K1429-1) as a template. PCR was carried out by using a commercially available kit (Clontech, Advantage 2 PCR Kit (#K1910)) and a PCR apparatus (Takara Shuzo, PCR Thermal Cycler MP) according to the attached protocol in a conventional manner.

The obtained PCR-amplified fragment was inserted into the pCR2.1 vector by using an Original TA Cloning Kit (Invitrogen, #K2000) according to the attached protocol and cloned in an *Escherichia coli* strain INValphaF'. The plasmid DNA was prepared by using Plasmid Mini Kit (QIAGEN) according to the manufacturer's protocol. The sequence of the obtained plasmid DNA was determined by performing a reaction using BigDye Terminator Cycle Sequencing FS Ready Reaction Kit (Applied Biosystems) and M13 Reverse Primer and the M13 Forward (−20) Primer according to the attached protocol and then performing electrophoresis by using 373S DNA Sequencer (Applied Biosystems).

Subsequently, 3' rapid amplification of cDNA ends (3' RACE) was carried out to obtain a cDNA region (3' end side) that was not included in the clone obtained as described above and the aforementioned EST clone. First, a primer having the nucleotide sequence of SEQ ID NO: 5 was prepared based on the sequence of the above-obtained cDNA fragment. Then, 3'-RACE-Ready cDNA was synthesized by using mRNA derived from the mouse testis (Clontech, #6612-1) as a template and SMART RACE cDNA Amplification Kit (Clontech, #K1811) according to the attached protocol. PCR amplification was performed by using the obtained cDNA, the aforementioned primers and PCR Thermal Cycler MP (Takara Shuzo) according to the protocol attached to the kit to obtain a cDNA fragment on the 3' end side of the target gene. The amplified fragment was cloned to obtain plasmid DNA by the aforementioned method, and its nucleotide sequence was determined. Thus, the cDNA sequence of the target gene having a substantially full length was determined except for a part on the 5' end side.

Subsequently, to identify a human homologue of the gene, the human EST database was searched based on an amino acid sequence estimated to be encoded by the above obtained mouse cDNA in the same manner as described above. As a result, one human EST clone (#AA620978) was obtained. As described above, it was considered that the sequence of this EST clone was not accurate either and did not include the coding region in its full length. Therefore, 3' RACE and 5' RACE were performed to obtain the target cDNA in the full length.

A primer for 3' RACE (SEQ ID NO: 6) and a primer for 5' RACE (SEQ ID NO: 7) were prepared. Then, 3'-RACE-Ready cDNA and 5'-RACE-Ready cDNA were synthesized by using mRNA derived from the human kidney (Clontech, #6538-1) as a template and SMART RACE cDNA Amplification Kit (Clontech, #K1811) according to the attached protocol. These cDNA were amplified by PCR using the aforementioned primers and PCR Thermal Cycler MP (Takara Shuzo) according to the protocol attached to the kit to obtain cDNA fragments on the 3' end side and 5' end side of the target gene. The amplified fragment was cloned to obtain plasmid DNA by the aforementioned method, and its nucleotide sequence was determined. Thus, the complete nucleotide sequence of the target gene and the amino acid sequence encoded by the gene were determined. These nucleotide sequence and amino acid sequence are shown in SEQ ID NOS: 1 and 2, respectively.

The amino acid sequence was searched by using the Simple Modular Architecture Research Tool (SMART, see Schulta, J., Copley, R. R., Doerks, T., Ponting, C. P., Bork, P., SMART: A web-based tool for the study of genetically mobile domains, Nucleic Acids Research, 28 (1), 231–234, 2000). As a result, it was found that the protein encoded by the aforementioned cDNA was constituted by a signal peptide, extracellular region, transmembrane region and intracellular region from the N-terminus side. Further, it was also found that the extracellular region was constituted by two immunoglobulin-like regions. Therefore, this protein is a protein molecule that exists on the cell surface and belongs to the immunoglobulin superfamily. This protein was designated as BT-IgSF.

Known proteins that show homology to the amino acid sequence of the BT-IgSF protein were searched by the aforementioned method (http://www.ncbi.nlm.nih.gov/BLAST/). As a result, as protein molecules having the highest homology at the amino acid level, there were found an endothelial cell-selective adhesion molecule (see Hirata, K., Ishida, T., Penta, K., Rezaee, M., Yang, E., Wohlgemuth, J., Quertermous, T., Cloning of an immunoglobulin family adhesion molecule selectively expressed by endothelial cells, Journal of Biological Chemistry, 276 (19), 16223–16231, 2001) and a receptor for coxsackie virus and adenovirus (see Bergelson, J. M., Cunningham, J. A., Droguett, G., Kurt-Jones, E. A., Krithivas, A., Hong, J. S., Horwitz, M. S., Crowell, R. L., Finberg, R. W., Isolation of a common receptor for coxsackie B viruses and adenoviruses 2 and 5, Science, 275, 1320–1323, 1997). However, both molecules showed homology of only about 30% to BT-IgSF at the amino acid level. Further, in the search at the nucleotide sequence level, no molecule showing significant homology was found (10% or lower).

<2> Analysis of BT-IgSF Gene Expression

In order to find the function of the BT-IgSF molecule, tissues in which the molecule was expressed were examined by using Human Multiple Tissue Expression Array (Clontech, #7775-1) by the Northern hybridization method. The hybridization was performed according to the protocol attached to the array, and the procedure is outlined below.

First, a cDNA probe including the entire coding region of cDNA of the human BT-IgSF gene was prepared. To this end, primers shown as SEQ ID NOS: 8 and 9 were prepared. A cDNA fragment derived from the human BT-IgSF gene was amplified by PCR using these primers and cDNA derived from the human kidney (Clontech, Catalog No. K1420-1) as a template. PCR was carried out by using Advantage 2 PCR Kit (Clontech, K1910) and PCR Thermal Cycler MP (Takara Shuzo) in a conventional manner according to the attached protocol. The obtained cDNA has one base of G at the 5' end and a sequence of GACATGAGG at the 3' end in addition to the sequence of SEQ ID NO: 1. This cDNA was labeled by using $^{32}$P-labeled dCTP (Amersham Pharmacia Biotech, #PB10205) and MegaPrime DNA Labeling System (Amersham-Pharmacia Biotech, #RPN1606) according to the manufacturer's protocol. Northern hybridization was carried out by using this labeled probe and Human Multiple Tissue Expression Array. The hybridization was performed overnight at 65° C. by using ExpressHyb Hybridization Solution (Clontech, #8015). Washing was performed four times with 2×SSC solution containing 1% SDS 65° C. for 20 minutes and twice with 0.1×SSC solution containing 0.5% SDS at 55° C. for 20 minutes.

As a result of the above experiment, it was found that expression of the BT-IgSF gene was substantially limited in the testis and the brain (FIG. 1). Expressions at various sites in the brain were further analyzed by using the aforementioned array, and it was found that the BT-IgSF gene was highly expressed especially in the corpus callosum (FIG. 1). Therefore, since the BT-IgSF protein has an extremely unique characteristic that its expression is limited in the corpus callosum and the testis, this protein is expected to function as a cell adhesion molecule involved in development of the corpus callosum and spermatogenesis.

What is claimed is:

1. A method for diagnosing increased risk of aplasia of the corpus callosum in a human subject, comprising the steps of: investigating the presence of a target gene, wherein said target gene encodes a polypeptide comprising the sequence of SEQ ID NO: 2; and diagnosing increased risk of aplasia of the corpus callosum when the presence of the target gene is not detected.

2. The method according to claim 1, wherein said target gene is detected using a hybridization probe, wherein the hybridization probe is selected from the group consisting of the DNA fragment which is produced by PCR using oligonucleotides of SEQ ID NOS: 8 and 9 as primers and human cDNA as template, and the DNA fragment which is produced by 3'RACE or 5' RACE using oligonucleotide of SEQ ID NO: 6 or 7 as 3' RACE primer and 5' RACE primer, respectively, and human mRNA as template, and a DNA which is defined in the following (a) or (b):
  (a) a DNA comprising the nucleotide sequence identical or fully complementary to the nucleotide numbers 67–1296 of SEQ ID NO: 1;
  (b) a DNA which is hybridizable with the nucleotide sequence identical or fully complementary to the nucleotide numbers 67 to 1296 of SEQ ID NO: 1 under stringent conditions, wherein stringent conditions are defined as hybridization at a salt concentration of 0.2×SSC, 0.1% SDS at 40° C.

3. A method for diagnosing increased risk of aplasia of the corpus callosum in a human subject, comprising the steps of:
  investigating the presence of a target gene, wherein said target gene encodes a polypeptide comprising the sequence of SEQ ID NO: 2 by hybridization using a hybridization probe which consists of a nucleotide sequence selected from the group consisting of SEQ ID NOS: 6, 7, 8, and 9, and
  diagnosing increased risk of aplasia of the corpus callosum when the presence of the target gene is not detected.

* * * * *

UNITED STATES PATENT AND TRADEMARK OFFICE
CERTIFICATE OF CORRECTION

PATENT NO.         : 7,217,524 B2
APPLICATION NO. : 11/409216
DATED              : May 15, 2007
INVENTOR(S)        : Suzu et al.

It is certified that error appears in the above-identified patent and that said Letters Patent is hereby corrected as shown below:

Column 20, Line 4, "at 40° C." should be changed to --at 42° C.--

Signed and Sealed this

Eighteenth Day of December, 2007

JON W. DUDAS
*Director of the United States Patent and Trademark Office*

SEQUENCE LISTING

<160> NUMBER OF SEQ ID NOS: 9

<210> SEQ ID NO 1
<211> LENGTH: 1296
<212> TYPE: DNA
<213> ORGANISM: Homo sapiens
<220> FEATURE:
<221> NAME/KEY: CDS
<222> LOCATION: (1)..(1296)
<220> FEATURE:
<221> NAME/KEY: sig_peptide
<222> LOCATION: (1)..(66)
<220> FEATURE:
<221> NAME/KEY: mat_peptide
<222> LOCATION: (67)..(1293)

<400> SEQUENCE: 1

```
atg act tct cag cgt tcc cct ctg gcg cct ttg ctg ctc ctc tct ctg        48
Met Thr Ser Gln Arg Ser Pro Leu Ala Pro Leu Leu Leu Leu Ser Leu
        -20                 -15                 -10 cac ggt gtt gca gca tcc ctg gaa gtg tca gag agc cct ggg agt atc        96
His Gly Val Ala Ala Ser Leu Glu Val Ser Glu Ser Pro Gly Ser Ile
     -5                  -1   1                   5                  10 cag gtg gcc cgg ggt cag aca gca gtc ctg ccc tgc act ttc act acc       144
Gln Val Ala Arg Gly Gln Thr Ala Val Leu Pro Cys Thr Phe Thr Thr
                     15                  20                  25 agc gct gcc ctc att aac ctc aat gtc att tgg atg gtc act cct ctc       192
Ser Ala Ala Leu Ile Asn Leu Asn Val Ile Trp Met Val Thr Pro Leu
                 30                  35                  40 tcc aat gcc aac caa cct gaa cag gtc atc ctg tat cag ggt gga cag       240
Ser Asn Ala Asn Gln Pro Glu Gln Val Ile Leu Tyr Gln Gly Gly Gln
             45                  50                  55 atg ttt gat ggt gcc ccc cgg ttc cac ggt agg gta gga ttt aca ggc       288
Met Phe Asp Gly Ala Pro Arg Phe His Gly Arg Val Gly Phe Thr Gly
         60                  65                  70 acc atg cca gct acc aat gtc tct atc ttc att aat aac act cag tta       336
Thr Met Pro Ala Thr Asn Val Ser Ile Phe Ile Asn Asn Thr Gln Leu
 75                  80                  85                  90 tca gac act ggc acc tac cag tgc ctg gtc aac aac ctt cca gac ata       384
Ser Asp Thr Gly Thr Tyr Gln Cys Leu Val Asn Asn Leu Pro Asp Ile
                 95                 100                 105 ggg ggc agg aac att ggg gtc acc ggt ctc aca gtg tta gtt ccc cct       432
Gly Gly Arg Asn Ile Gly Val Thr Gly Leu Thr Val Leu Val Pro Pro
             110                 115                 120 tct gcc cca cac tgc caa atc caa gga tcc cag gat att ggc agc gat       480
Ser Ala Pro His Cys Gln Ile Gln Gly Ser Gln Asp Ile Gly Ser Asp
         125                 130                 135 gtc atc ctg ctc tgt agc tca gag gaa ggc att cct cga cca act tac       528
Val Ile Leu Leu Cys Ser Ser Glu Glu Gly Ile Pro Arg Pro Thr Tyr
     140                 145                 150 ctt tgg gag aag tta gac aat acc ctc aaa cta cct cca aca gct act       576
Leu Trp Glu Lys Leu Asp Asn Thr Leu Lys Leu Pro Pro Thr Ala Thr
155                 160                 165                 170 cag gac cag gtc cag gga aca gtc acc atc cgg aac atc agt gcc ctg       624
Gln Asp Gln Val Gln Gly Thr Val Thr Ile Arg Asn Ile Ser Ala Leu
                 175                 180                 185 tct tca ggt ttg tac cag tgc gtg gct tct aat gct att gga acc agc       672
Ser Ser Gly Leu Tyr Gln Cys Val Ala Ser Asn Ala Ile Gly Thr Ser
             190                 195                 200 acc tgt ctt ctg gat ctc cag gtt att tca ccc cag ccc agg aac att       720
Thr Cys Leu Leu Asp Leu Gln Val Ile Ser Pro Gln Pro Arg Asn Ile
```

```
gga cta ata gct gga gcc att ggc act ggt gca gtt att atc att ttt      768
Gly Leu Ile Ala Gly Ala Ile Gly Thr Gly Ala Val Ile Ile Ile Phe
    220                 225                 230 tgc att gca cta att tta ggg gca ttc ttt tac tgg aga agc aaa aat      816
Cys Ile Ala Leu Ile Leu Gly Ala Phe Phe Tyr Trp Arg Ser Lys Asn
235                 240                 245                 250 aaa gag gag gaa gaa gaa gaa att cct aat gaa ata aga gag gat gat      864
Lys Glu Glu Glu Glu Glu Glu Ile Pro Asn Glu Ile Arg Glu Asp Asp
                    255                 260                 265 ctt cca ccc aag tgt tct tct gcc aaa gca ttt cac act gag att tcc     912
Leu Pro Pro Lys Cys Ser Ser Ala Lys Ala Phe His Thr Glu Ile Ser
                270                 275                 280 tcc tcg gac aac aac aca cta acc tct tcc aat gcc tac aac agt cga     960
Ser Ser Asp Asn Asn Thr Leu Thr Ser Ser Asn Ala Tyr Asn Ser Arg
            285                 290                 295 tac tgg agc aac aat cca aaa gtt cat aga aac aca gag tca gtc agc    1008
Tyr Trp Ser Asn Asn Pro Lys Val His Arg Asn Thr Glu Ser Val Ser
300                 305                 310 cac ttc agt gac ttg ggc caa tct ttc tct ttc cac tca ggc aat gcc    1056
His Phe Ser Asp Leu Gly Gln Ser Phe Ser Phe His Ser Gly Asn Ala
315                 320                 325                 330 aac ata cca tcc att tat gct aat ggg acc cat ctg gtc ccg ggt caa    1104
Asn Ile Pro Ser Ile Tyr Ala Asn Gly Thr His Leu Val Pro Gly Gln
                335                 340                 345 cat aag act ctg gta gtg aca gcc aac aga ggg tca tca cca cag gtg    1152
His Lys Thr Leu Val Val Thr Ala Asn Arg Gly Ser Ser Pro Gln Val
            350                 355                 360 atg tcc agg agc aat ggc tca gtc agt agg aag cct cgg cct cca cac    1200
Met Ser Arg Ser Asn Gly Ser Val Ser Arg Lys Pro Arg Pro Pro His
        365                 370                 375 act cat tcc tac acc atc agc cac gca aca ctg gaa cga att ggt gca    1248
Thr His Ser Tyr Thr Ile Ser His Ala Thr Leu Glu Arg Ile Gly Ala
    380                 385                 390 gta cct gtc atg gta cca gcc cag agt cgg gcc ggg tcc ttg gta tag    1296
Val Pro Val Met Val Pro Ala Gln Ser Arg Ala Gly Ser Leu Val
395                 400                 405
```

<210> SEQ ID NO 2
<211> LENGTH: 431
<212> TYPE: PRT
<213> ORGANISM: Homo sapiens

<400> SEQUENCE: 2

```
Met Thr Ser Gln Arg Ser Pro Leu Ala Pro Leu Leu Leu Leu Ser Leu
        -20                 -15                 -10

His Gly Val Ala Ala Ser Leu Glu Val Ser Glu Ser Pro Gly Ser Ile
     -5                  -1  1                   5                  10

Gln Val Ala Arg Gly Gln Thr Ala Val Leu Pro Cys Thr Phe Thr Thr
                    15                  20                  25

Ser Ala Ala Leu Ile Asn Leu Asn Val Ile Trp Met Val Thr Pro Leu
                30                  35                  40

Ser Asn Ala Asn Gln Pro Glu Gln Val Ile Leu Tyr Gln Gly Gly Gln
            45                  50                  55

Met Phe Asp Gly Ala Pro Arg Phe His Gly Arg Val Gly Phe Thr Gly
        60                  65                  70

Thr Met Pro Ala Thr Asn Val Ser Ile Phe Ile Asn Asn Thr Gln Leu
    75                  80                  85                  90
```

```
Ser Asp Thr Gly Thr Tyr Gln Cys Leu Val Asn Asn Leu Pro Asp Ile
                    95                 100                105
Gly Gly Arg Asn Ile Gly Val Thr Gly Leu Thr Val Leu Val Pro Pro
            110             115                 120
Ser Ala Pro His Cys Gln Ile Gln Gly Ser Gln Asp Ile Gly Ser Asp
            125             130                 135
Val Ile Leu Leu Cys Ser Ser Glu Gly Ile Pro Arg Pro Thr Tyr
140             145                 150
Leu Trp Glu Lys Leu Asp Asn Thr Leu Lys Leu Pro Pro Thr Ala Thr
155             160                 165                170
Gln Asp Gln Val Gln Gly Thr Val Thr Ile Arg Asn Ile Ser Ala Leu
                175             180                 185
Ser Ser Gly Leu Tyr Gln Cys Val Ala Ser Asn Ala Ile Gly Thr Ser
            190             195                 200
Thr Cys Leu Leu Asp Leu Gln Val Ile Ser Pro Gln Pro Arg Asn Ile
            205             210                 215
Gly Leu Ile Ala Gly Ala Ile Gly Thr Gly Ala Val Ile Ile Ile Phe
    220             225                 230
Cys Ile Ala Leu Ile Leu Gly Ala Phe Phe Tyr Trp Arg Ser Lys Asn
235             240                 245                250
Lys Glu Glu Glu Glu Glu Ile Pro Asn Glu Ile Arg Glu Asp Asp
                255             260                 265
Leu Pro Pro Lys Cys Ser Ser Ala Lys Ala Phe His Thr Glu Ile Ser
            270             275                 280
Ser Ser Asp Asn Asn Thr Leu Thr Ser Ser Asn Ala Tyr Asn Ser Arg
            285             290                 295
Tyr Trp Ser Asn Asn Pro Lys Val His Arg Asn Thr Glu Ser Val Ser
            300             305                 310
His Phe Ser Asp Leu Gly Gln Ser Phe Ser Phe His Ser Gly Asn Ala
315             320                 325                330
Asn Ile Pro Ser Ile Tyr Ala Asn Gly Thr His Leu Val Pro Gly Gln
            335             340                 345
His Lys Thr Leu Val Val Thr Ala Asn Arg Gly Ser Ser Pro Gln Val
            350             355                 360
Met Ser Arg Ser Asn Gly Ser Val Ser Arg Lys Pro Arg Pro His
            365             370                 375
Thr His Ser Tyr Thr Ile Ser His Ala Thr Leu Glu Arg Ile Gly Ala
    380             385                 390
Val Pro Val Met Val Pro Ala Gln Ser Arg Ala Gly Ser Leu Val
395             400                 405
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence : an artificially synthesized primer sequence

<400> SEQUENCE: 3
gtgtcgcaag atccctggaa gtgtc                                    25

<210> SEQ ID NO 4
<211> LENGTH: 25
<212> TYPE: DNA
<213> ORGANISM: Artificial Sequence
<220> FEATURE:

```
<223> OTHER INFORMATION: Description of Artificial Sequence : an
      artificially synthesized primer sequence

<400> SEQUENCE: 4
ccttggattt ggcattgtgg agcag                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence : an
      artificially synthesized primer sequence

<400> SEQUENCE: 5
agacagaggg ggcagaaaca tcggg                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence : an
      artificially synthesized primer sequence

<400> SEQUENCE: 6
cttctgcccc acaatgccaa atcca                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence : an
      artificially synthesized primer sequence

<400> SEQUENCE: 7
cgactgttgt aggcattgga agagg                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence : an
      artificially synthesized primer sequence

<400> SEQUENCE: 8
gatgacttct cagcgttccc ctctg                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence : an
      artificially synthesized primer sequence

<400> SEQUENCE: 9
cctcatgtcc tataccaagg acccg                                              25
```